United States Patent [19]

Satoh

[11] Patent Number: 4,651,723

[45] Date of Patent: Mar. 24, 1987

[54] DROP FOOT SPLINT

[75] Inventor: Kohji Satoh, Utsunomiya, Japan

[73] Assignee: Kyowa Gishi Kogyo Kabushiki Kaisha, Utsunomiya, Japan

[21] Appl. No.: 842,844

[22] Filed: Mar. 24, 1986

[51] Int. Cl.[4] ............................................. A61F 5/00
[52] U.S. Cl. .................................................. 128/80 E
[58] Field of Search ................... 128/80 E, 80 H, 80 J, 128/80 R, 87 R, 83, 83.5, 85

[56] References Cited

U.S. PATENT DOCUMENTS 3,986,501 10/1976 Schad ................................ 128/80 E

OTHER PUBLICATIONS

Bunch, W.; Principles of Orthotic Treatment C. V. Mosby Co. Saint Louis 1976, pp. 41–44.
Improved Short Caliper for Spasticity in Production, Perlstein Type, Nov. 9, 1950, Pope Foundation, Inc.

Primary Examiner—Robert A. Hafer
Assistant Examiner—Kathleen J. D'Arrigo
Attorney, Agent, or Firm—Wenderoth, Lind & Ponack

[57] ABSTRACT

A ringed flexible leather brace has fastenings at each end portion. A rectangular hard leather including a stepped periphery and a longitudinal slender guide groove is integrally and vertically mounted on the face of the ringed brace and in the vicinity of one fastening to form a longitudinal slender and thin socket having a bottom opening. A first separable fastener is vertically attached on the rear side and at the corresponding portion of the socket. A bent plate spring having a straight upper portion, a straight lower portion and also an elastic belt including a second separable fastener is slidably inserted into the socket through the bottom opening to form a slidable engagement with the ringed brace.

3 Claims, 11 Drawing Figures

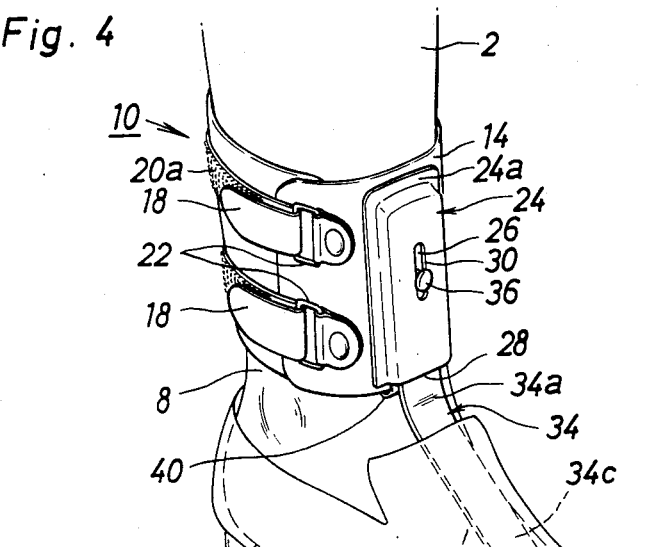
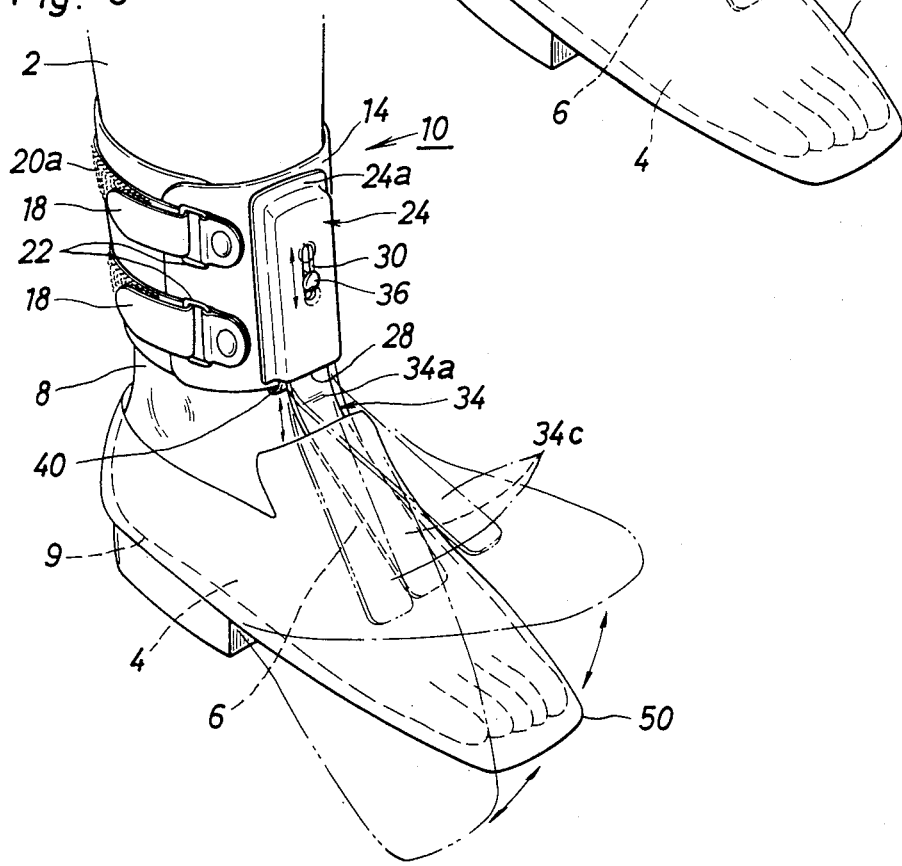

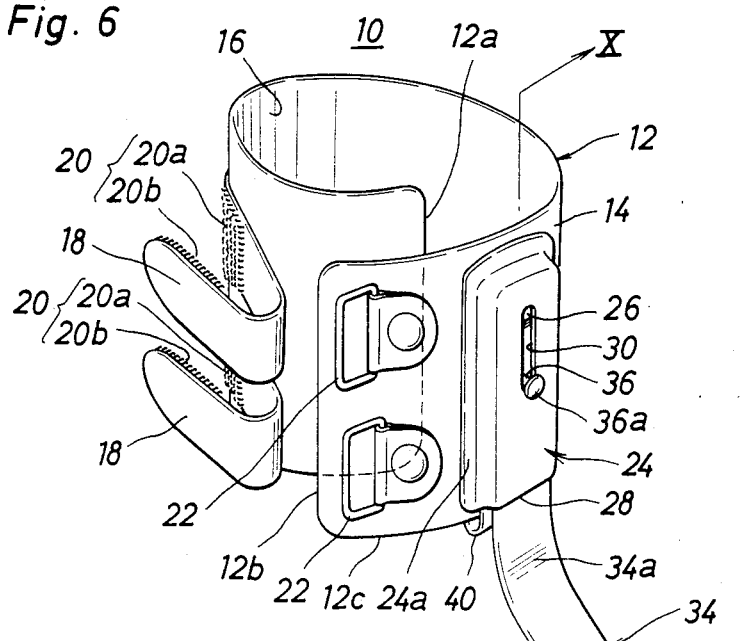
Fig. 6
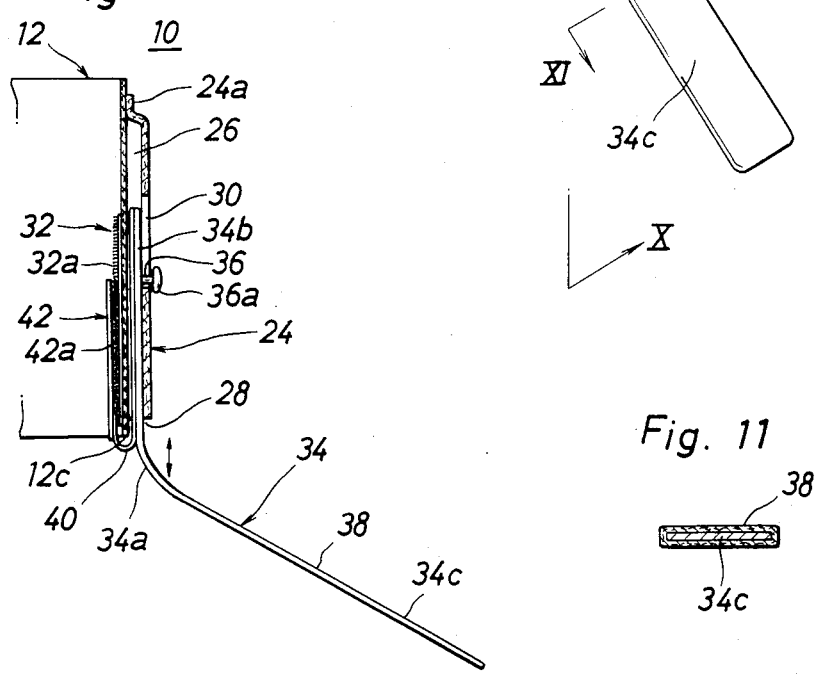
Fig. 10
Fig. 11

DROP FOOT SPLINT

BACKGROUND OF THE INVENTION

This invention relates to improvements in a drop foot splint, and more particularly to an improved drop foot splint which enables a paralyzed person on his one side to walk comfortably and safely.

A patient who has suffered from either cerebral paralysis or cerebral thrombosis is usually paralyzed on his one side of the body so as to cause a drop foot as shown in FIG. 1.

There is already known a protective arrangement for the drop foot of a paralyzed person on his one side. As shown in FIGS. 2 and 3, this arrangement comprises a leather brace 12, an L-shaped plate spring 34 integrally secured to the brace 12 and a pair of fastenings 20, wherein the L-shaped plate spring 34 inserted between the shoe 50 and the instep 6 of the foot 4 is always kept immobile relative to the brace 12 so that when the foot 4 is bent to the ankle 8 during walking, i.e. the angle of the ankle 8 with the instep 6 of the foot 4 is made acute, the horizontal portion of the L-shaped plate spring 34 is forcedly brought into contact with the instep 6 so as to cause an oppressible pain to the instep 6, much more giving an intolerable acute pain while climbing or going down the stairs.

In addition, during climbing or going down the stairs, angular bending movements of the ankle 8 wearing the conventional drop foot splint shown in FIGS. 2 and 3 cause discomfort and abrasions and also tire the ankle and the foot.

OBJECTS OF THE INVENTION

A principal object of this invention is to provide an improved drop foot splint wound around the ankle of a paralyzed person on his one side whereby a bent plate spring of the splint can be slidably brought into contact with the ankle and instep to assure both correct protection and the retention of the drop foot.

Another object of this invention is to provide an improved drop foot splint whereby the wearer of the drop foot splint can walk comfortably and safely.

Another object of this invention is to provide an improved drop foot splint whereby a bent plate spring of the splint can follow the angular bending movements of the ankle so as to fit the slidable bent plate spring along the angular portion between the ankle and the instep of the wearer.

Another object of this invention is to provide an improved drop foot splint whereby the wearer of the drop foot splint can walk up or go down the stairs or slopes without causing any oppressive pain to the instep and tiring the ankle and foot.

Another object of this invention is to provide a drop foot splint whereby slidable engagement of the bent plate spring into the brace facilitates, during bending of the foot, longitudinal slidable reciprocation of the plate spring and does not impede the bending function of the foot relative to the ankle.

A further object of this invention is to provide an improved drop foot splint which can be easily wound around the ankle of a paralyzed person on his one side.

Still another object of this invention is to provide a device suitable for the aforementioned purposes which is simple in construction and at the same time rigid, strong and durable.

BRIEF DESCRIPTION OF DRAWINGS

While I have shown in the accompanying drawings a preferred embodiment of my invention, it should be understood that the same is susceptible of modification and change without departing from the spirit of my invention.

Referring to the drawings,

FIG. 4 is a perspective view of the drop foot wearing the splint of this invention;

FIG. 5 is a view similar to FIG. 4 and showing the foot being bent relative to the ankle during walking;

FIG. 6 is a perspective view of the drop foot splint taken off the drop foot;

FIG. 10 is an enlarged longitudinal sectional view of FIG. 6 taken on line X—X and showing the bent plate spring; and FIG. 11 is an enlarged horizontal sectional view of FIG. 6 taken on line XI—XI.

Figure 1:
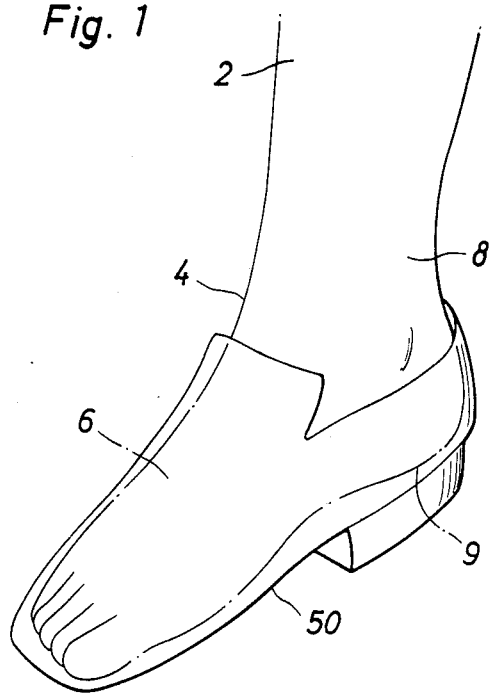
FIG. 1 a perspective view of a drop foot wearing a shoe.
Figure 2:
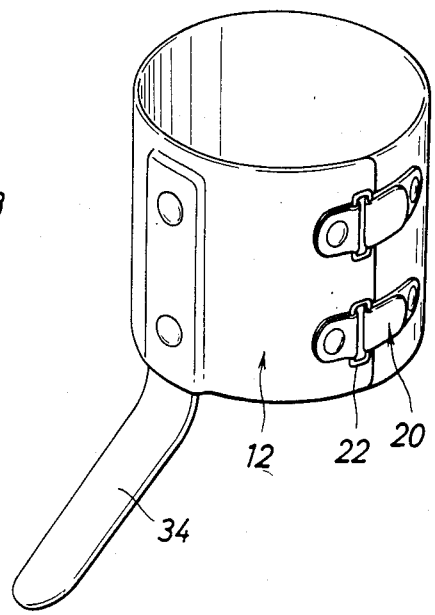
FIG. 2 is a perspective view of a conventional drop foot splint.
Figure 3:
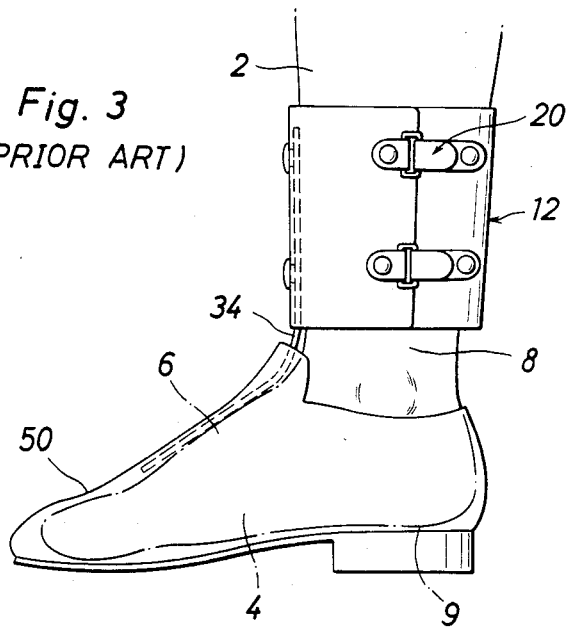
FIG. 3 is a side elevation of the drop foot wearing the conventional drop foot splint and the shoe.
Figure 7:
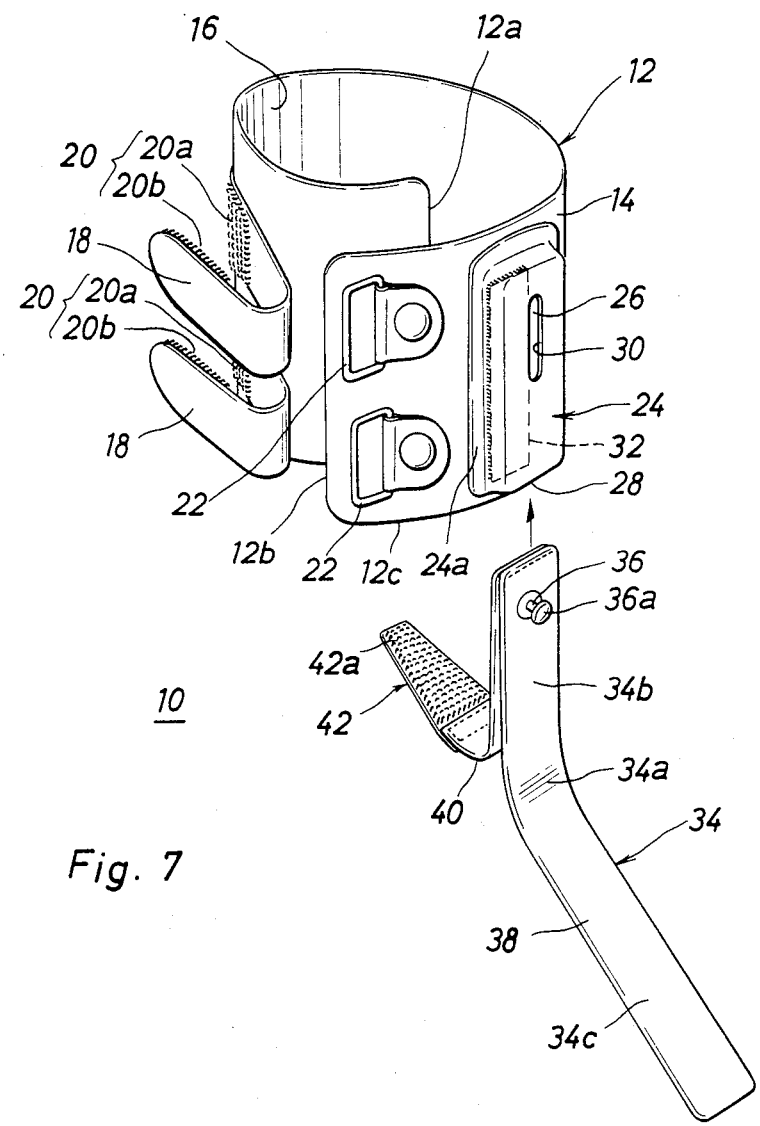
FIG. 7 is a view similar to FIG. 6 and showing a bent plate spring taken out of a socket of the drop foot splint.

In the illustrative embodiment of FIGS. 4–11, there is shown the application of the drop foot splint 10 wound around an ankle designated by reference numeral 8. The splint 10 comprises a brace 12 and a bent plate spring 34 which is slidably attached into the brace 12.

The brace 12 may for example be of retangular flexible leather which is shaped into a ring to wind around the ankle 8 of a person paralyzed on his one side.

A pair of leather belts 18 are at each end portion horizontally and parallelly secured at portions a little to one end portion 12a from the middle portion of the ringed brace 12.

Figure 8:
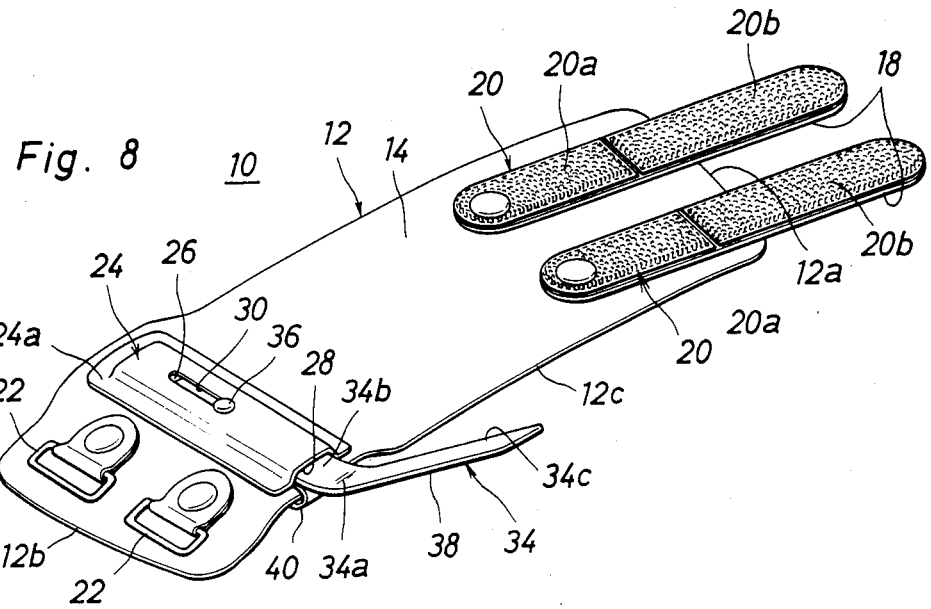
FIG. 8 is a perspective view from the surface and showing the spread ringed brace.
Figure 9:
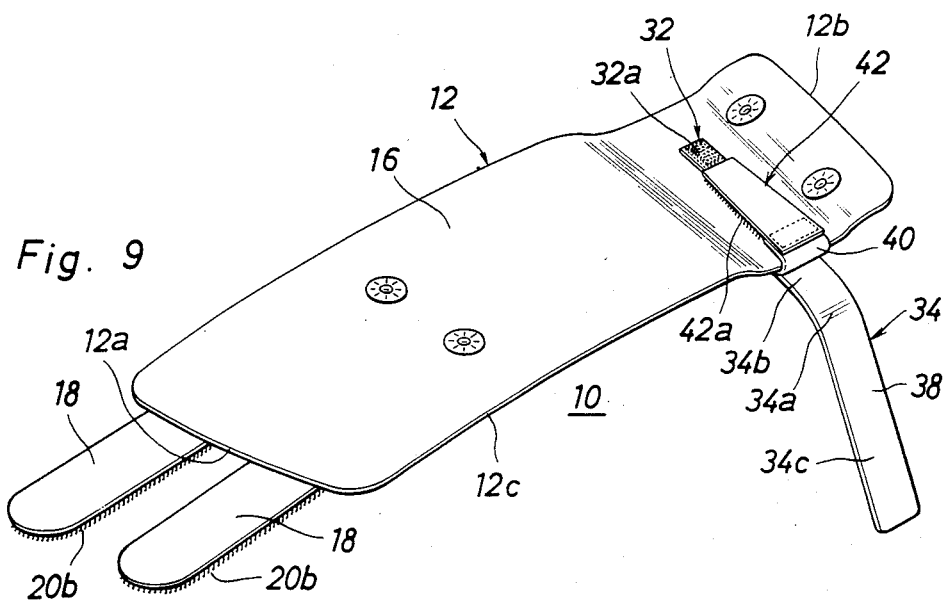
FIG. 9 is a perspective view from the rear side, similar to FIG. 8.

A press-on and pull-off separable fastener 20 including a large number of closely spaced fastening elements 20a on one half portion and a large number of closely spaced complementary fastening elements 20b on another half portion is integrally mounted on the face of each leather belt 18 as shown in FIG. 8.

A pair of metal clasps 22 are fixed on the face 14 and at the corresponding portion of another end portion 12b of the ringed brace 12.

As particularly shown in FIGS. 4–6, a rectangular hard leather 24 having a stepped periphery 24a is integrally and vertically mounted on the face 14 of the ringed brace 12 and in the vicinity of the metal clasps 22 to form a longitudinally slender and thin socket 26, which has a bottom opening 28 and a longitudinal slender guide groove 30 at a middle portion of the hard leather 24.

A first press-on and pull-off separable fastener 32 including a large number of closely spaced fastening elements 32a is integrally and vertically attached on the rear side 16 of the ringed brace 12 and at the corresponding portion of the socket 26.

A steel plate spring 34 is bent at its middle portion 34a to divide into a straight upper portion 34b and a straight lower portion 34c which are substantially coincided with the angle between the ankle 8 and the instep 6 of the wearer. A steel knob 36 is provided on the face 14 and near a top portion of the straight upper portion 34b, and a leather 38 is wholly covered on the plate spring 34 to partially project the knob 36 through an opening of the leather 38.

An end portion of an elastic belt 40 is fixed at the top portion of the straight upper portion 34b to extend longitudinally into a rear side of the straight upper portion 34b.

An end portion of a second separable fastener 42 including a large number of closely spaced fastening elements 42a is secured at a lower end portion of the elastic belt 40.

The straight upper portion 34b of the bent plate spring 34 including the elastic belt 40 is slidably inserted into the socket 26 to project the knob 36 partially through the longitudinal slender guide groove 30, and the second separable fastener 42 is folded over a lower edge of the ringed brace 12. When the second separable fastener 42 is simply pressed on the first separable fastener 32, the former is engaged with the latter in a face-to-face relationship to join the bent plate spring 34 into the socket 26 of the retangular hard leather 24 and also to locate the knob 36 at the lowest portion of the guide groove 30. In this way, the bent plate spring 34 is slidably engaged into the socket 26 of the ringed brace 12.

For wearing the drop foot splint 10, the shoe 50 is put one, the straight lower portion 34c of the steel plate spring 34 is inserted into between the shoe 50 and the instep 6 of the foot 4, the ringed brace 12 is wound around the ankle 8, and finally the end portions 12a and 12b are fastened by the fasteners 18 and the metal clasps 22 as shown in FIGS. 4 and 5, thus lifting and correcting the drop foot 4 wearing the shoe 50 in a normal position.

During walking, with angular bending movements of the foot 4 with respect to the ankle 8, the bent plate spring 34 can reciprocate slidably within the socket 26 as shown by an arrow, i.e. with the increase of the bending angle between the foot 4 or brought down by the restoring moment of the elastic belt. The knob 36 can slide within the guide groove 30 with its head 36a partially projecting through the guide groove 30.

The bent plate spring 34 slidably engaged into the socket 26 of the ringed brace 12 is adjusted to the angular bending movements of the foot 4 relative to the ankle 8, thus making angular bending movements of the foot 4 much easier during walking. At the same time, the lower portion 34c of the bent plate spring 34 does not give the oppressible pain to the instep 6, but facilitate comfortable and safe walking of the drop foot wearer.

It will be understood that the invention is not limited to the illustrative embodiments described and shown above, which may have other variations or adaptations without thereby departing from the scope of the appended claims.

I claim:

1. An improved splint for application of a drop foot and for correct retention of the drop foot relative to an ankle of a paralyzed person on his one side, comprising:
   a flexible ringed brace to be wound around the ankle;
   a pair of leather belts secured horizontally and parallelly at one end portion a little toward one end portion from the middle portion of the ringed brace, said each belt including a separable fastener integrally mounted on the face and said separable fastener having a large number of closely spaced fastening elements on one half portion and a large number of closely spaced complementary fastening elements on another half portion;
   a pair of metal clasps fixed on the face and at the corresponding portions of another end portion of said ringed brace for engagement with said fasteners;
   a rectangular hard member having a stepped periphery and vertically mounted on the face of said ringed brace and in vicinity of said metal clasps to form a longitudinally slender and thin socket, said hard member having a bottom opening and a longitudinal slender guide groove at a middle portion thereof;
   a first separable fastener vertically mounted on the rear side and at the corresponding portion of said socket;
   a plate spring bent at its middle portion to divide into a straight upper portion and a straight lower portion which are substantially coincided with the angle between the ankle and the instep of the wearer, said straight upper portion including a knob on the face and near a top portion of said straight upper portion, and said plate spring covered wholly with a leather to project partially through an opening of the leather;
   an elastic belt having its one end secured at the top portion of said straight upper portion to extend longitudinally into a rear side thereof, and a second separable fastener having its one end secured at a lower portion of said elastic belt, said straight upper portion of the bent plate spring and said elastic belt being slidably inserted into the socket to project the knob partially through the slender guide groove, and said flexible belt being folded over the lower edge of the ringed brace to make said second separable fastener engage in a face-to-face relationship with said first separable fastener, thus forming a slidable engagement into the socket of said ringed brace.

2. A drop foot splint as claimed in claim 1, wherein the second separable fastener folded over a lower edge of the ringed brace is simply pressed on the first separable fastener to engage with said first separable fastener and always to locate the knob of the upper portion of the bent plate spring at the lowest portion of the guide groove by elasticity of the elastic belt.

3. A drop foot splint as claimed in claim 1, the bent plate spring is slidably reciprocated within the socket by the angular bending movements of the foot and the restoring moment of the elastic belt and with its knob projecting partially through the guide groove of said rectangular hard leather.

* * * * *